US012721618B2

(12) United States Patent
Medoff

(10) Patent No.: US 12,721,618 B2
(45) Date of Patent: Sep. 1, 2026

(54) METHOD AND APPARATUS FOR SUPPORTING A U-SHAPED PORTION OF AN ELONGATE FLEXIBLE ELEMENT RELATIVE TO A HUMAN BODY TISSUE

(71) Applicant: TriMed, Incorporated, Santa Clarita, CA (US)

(72) Inventor: Robert Medoff, Kailua, HI (US)

(73) Assignee: TriMed, Inc., Santa Clarita, CA (US)

( * ) Notice: Subject to any disclaimer, the term of this patent is extended or adjusted under 35 U.S.C. 154(b) by 924 days.

(21) Appl. No.: 17/132,144

(22) Filed: Dec. 23, 2020

(65) Prior Publication Data

US 2021/0196259 A1 Jul. 1, 2021

Related U.S. Application Data

(60) Provisional application No. 62/953,692, filed on Dec. 26, 2019.

(51) Int. Cl.

*A61B 17/04* (2006.01)
*A61B 17/06* (2006.01)
*A61B 90/00* (2016.01)

(52) U.S. Cl.

CPC ...... *A61B 17/0466* (2013.01); *A61B 17/0483* (2013.01); *A61B 17/06061* (2013.01); *A61B 2017/0404* (2013.01); *A61B 2017/0406* (2013.01); *A61B 2017/0409* (2013.01); *A61B 2090/037* (2016.02)

(58) Field of Classification Search

CPC ............ A61B 17/0466; A61B 17/0483; A61B 17/06061; A61B 2017/0404; A61B 2017/0406; A61B 2017/0409; A61B 2017/0414; A61B 2017/0417;

(Continued)

(56) References Cited

U.S. PATENT DOCUMENTS

| | | | |
|---|---|---|---|
| 1,322,410 | A | 11/1919 | Connelly |
| 1,806,162 | A | 5/1931 | Hahn |

(Continued)

FOREIGN PATENT DOCUMENTS

| | | |
|---|---|---|
| EP | 0934037 B1 | 12/2003 |
| WO | 2019/219548 A1 | 11/2019 |

OTHER PUBLICATIONS

International Search Report and Written Opinion, mailed Mar. 17, 2021 in International Patent Application No. PCT/US20/66793.

(Continued)

*Primary Examiner* — Tan-Uyen T Ho

(74) *Attorney, Agent, or Firm* — Wood, Phillips, Katz, Clark & Mortimer

(57) ABSTRACT

An apparatus and a method of engaging a U-shaped portion of an elongate flexible element with the apparatus. The apparatus has a body with an anchoring part, a channel extending up to the anchoring part, and an entry opening to the channel. With the U-shaped portion and body in an operative relationship, wherein the U-shaped portion straddles the anchoring part, the elongate flexible element can be tensioned to draw a side of the body against tissue. With the U-shaped portion straddling the anchoring part, the body can be reconfigured to change the size and/or shape of the entry opening and/or channel to avoid separation of part or all of the U-shaped portion from the body.

3 Claims, 6 Drawing Sheets

(58) Field of Classification Search
CPC .... A61B 2017/0427; A61B 2017/0438; A61B 2090/037; A61B 17/0401
See application file for complete search history.

(56) References Cited

U.S. PATENT DOCUMENTS

| | | | | |
|---|---|---|---|---|
| 2,025,663 | A | 12/1935 | Iuliano | |
| 2,095,340 | A | 10/1937 | Meyer | |
| 3,409,014 | A | 11/1968 | Shannon | |
| 4,823,794 | A | 4/1989 | Pierce | |
| 5,647,836 | A * | 7/1997 | Blake, III | A61F 2/0036 600/30 |
| 5,683,418 | A | 11/1997 | Luscombe et al. | |
| 5,961,538 | A | 10/1999 | Pedlick et al. | |
| 6,099,553 | A | 8/2000 | Hart et al. | |
| 6,270,518 | B1 | 8/2001 | Pedlick et al. | |
| 6,652,561 | B1 | 11/2003 | Tran | |
| 7,150,757 | B2 | 12/2006 | Fallin et al. | |
| 7,566,339 | B2 | 7/2009 | Fallin et al. | |
| 7,594,923 | B2 | 9/2009 | Fallin et al. | |
| 7,682,374 | B2 | 3/2010 | Foerster et al. | |
| 7,722,644 | B2 | 5/2010 | Fallin et al. | |
| 7,806,909 | B2 | 10/2010 | Fallin et al. | |
| 7,862,584 | B2 | 1/2011 | Lyons et al. | |
| 7,882,600 | B2 | 2/2011 | Judd | |
| 8,187,301 | B2 | 5/2012 | Lyons et al. | |
| 8,388,655 | B2 | 3/2013 | Fallin et al. | |
| 8,454,635 | B2 | 6/2013 | Paolitto et al. | |
| 8,591,578 | B2 | 11/2013 | Albertorio et al. | |
| 8,734,491 | B2 * | 5/2014 | Seavey | A61B 17/683 606/232 |
| 9,265,498 | B2 | 2/2016 | Fallin et al. | |
| 9,421,007 | B2 | 8/2016 | Brady et al. | |
| 9,498,202 | B2 | 11/2016 | Jafari et al. | |
| 9,642,610 | B2 | 5/2017 | Albertorio et al. | |
| 9,918,711 | B2 | 3/2018 | Seavey | |
| 10,022,122 | B2 | 7/2018 | Singhatat et al. | |
| 10,085,740 | B1 | 10/2018 | Anderson | |
| 10,215,258 | B2 | 2/2019 | Hintz et al. | |
| 10,299,784 | B2 | 5/2019 | Anderson | |
| 10,470,759 | B2 | 11/2019 | Miraki et al. | |
| 2004/0098053 | A1 | 5/2004 | Tran | |
| 2006/0190041 | A1 | 8/2006 | Fallin et al. | |
| 2008/0228881 | A1 | 9/2008 | Reynolds | |
| 2009/0143821 | A1 | 6/2009 | Stupak | |
| 2010/0211075 | A1 | 8/2010 | Stone | |
| 2010/0305585 | A1 | 12/2010 | Fallin et al. | |
| 2013/0245686 | A1 | 9/2013 | Fallin et al. | |
| 2018/0271522 | A1 | 9/2018 | Vedoff | |
| 2019/0029665 | A1 | 1/2019 | Anderson | |
| 2019/0380692 | A1 * | 12/2019 | Brazil | A61B 17/0401 |
| 2020/0146667 | A1 * | 5/2020 | Montross | A61B 17/0401 |

OTHER PUBLICATIONS

Supplementary Partial European Search Report mailed Dec. 4, 2023, in European Patent Application No. EP 20 90 6744.

* cited by examiner

Fig. 16
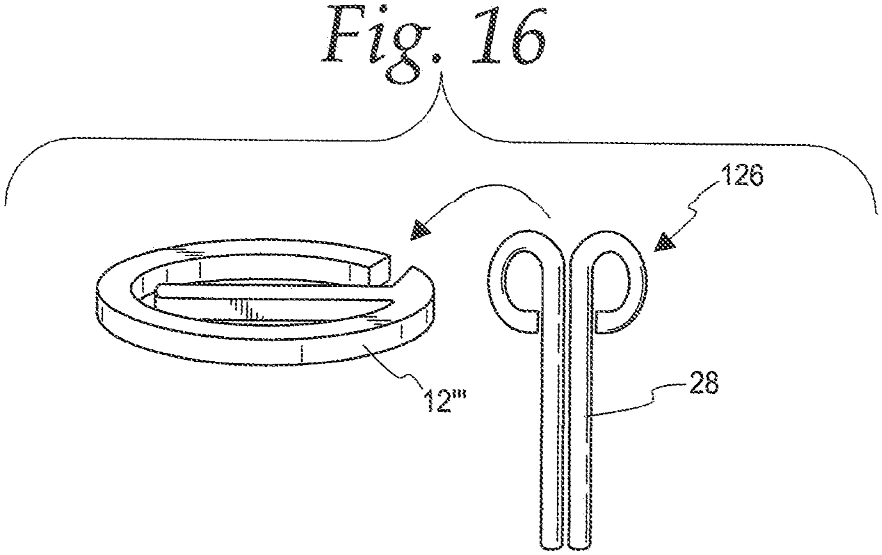
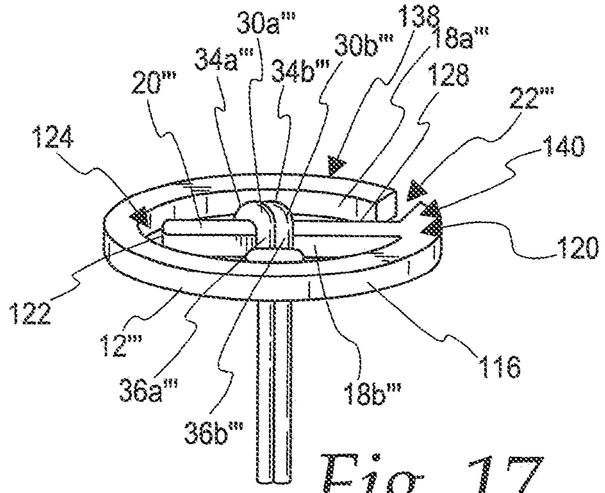
Fig. 17
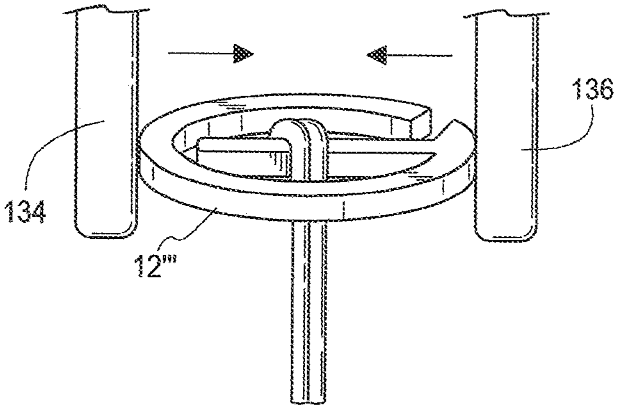
Fig. 18
126
12'''
28
30a'''
138
34a'''
30b'''
18a'''
20'''
34b'''
128
22'''
124
140
120
122
12'''
116
36a'''
18b'''
36b'''
136
134
12'''

METHOD AND APPARATUS FOR SUPPORTING A U-SHAPED PORTION OF AN ELONGATE FLEXIBLE ELEMENT RELATIVE TO A HUMAN BODY TISSUE

CROSS-REFERENCE TO RELATED APPLICATIONS

This is a non-provisional application claiming priority to U.S. Provisional Application No. 62/953,692, filed Dec. 26, 2019, which is incorporated herein by reference.

BACKGROUND OF THE INVENTION

Field of the Invention

This invention relates to elongate flexible elements directed into passages through human body tissue and, more particularly, to a method and apparatus for engaging a portion of the elongate flexible element exposed on one side of the tissue to prevent drawing of the exposed portion of the elongate flexible element into and through the passage.

Background Art

Many different surgical procedures are performed using an elongate flexible element that projects from a tissue passage at one side thereof wherein movement of the projecting portion of the flexible element back into the passage, as would permit withdrawal thereof, must be prevented. Such procedures are performed utilizing sutures and other types of elongate flexible elements.

One conventional way of preventing withdrawal of the projecting flexible element portion is to place one or more bodies at the side of the tissue and cause the projecting portion of the flexible element to bear against the body/bodies. The geometry of the body prevents the body in its operative position from moving into the passage. The body thus performs a bracing function and also distributes forces generated by the projecting portion of the flexible element over a larger area to avoid a stress concentration that might lead to compromising of the issue.

While the invention herein is concerned with procedures involving many different types of elongate flexible elements, the description herein will be focused upon an elongate flexible element in the form of a suture, with it being understood that this is only exemplary in nature and that the analysis of the prior art and the invention relates similarly to different types of elongate flexible element.

Similarly, the reference to "tissue" is not limited to either hard or soft tissue. Procedures may involve directing a suture through a single tissue that is either hard or soft, or a combination of tissues that are all hard or soft, or a combination thereof.

In many such conventional procedures, a far "button" is placed at the side of the tissue from which the suture projects whereat the projecting suture portion is required to be controlled. It is known to place the suture in an operative position with respect to the button and to direct the button through a passage in the tissue to expose the same and the suture portion carried therewith at the tissue side where the suture is to be controlled. While the button may be strategically designed so that it can move through a relatively small passage in one orientation and be placed in another orientation to span the passage to prevent withdrawal therefrom, in a best case, the passage required to accommodate the button must be relatively large. This can be a problem, particularly with procedures where such a passage formation may make a particular bone prone to fracture. Further, small bones may not lend themselves to being formed with a diameter substantial enough to allow this type of button to be passed therethrough. Generally it is an objective in all procedures to minimize the required size of the passage through which the suture extends.

With this latter objective in mind, many procedures are performed by directing only a suture through a passage to be exposed at a side whereat a button or other weight distributing or securing structure is attached. One common practice is to configure the suture so that a U-shaped portion projects from the passage at the tissue side at which control of the suture is required. This can be accomplished by doubling the suture against itself and advancing the formed suture through the passage with the "U" shape opening in a trailing direction. In one form, this involves forming a continuous loop which is directed through the passage until the leading end of the loop becomes exposed in the "U" shape. Thereafter, the button is attached from the side at which the suture protrudes.

In designing this far button, there are a number of objectives that must be considered that are often competing with each other. First of all, the surgeon wants a structure that can be easily and consistently connected to the suture. At the same time, the connection must have a high level of integrity. The first objective, if not met, creates inefficiency in procedures, becomes frustrating to surgeons, and can lead to an increase in fatigue. The latter objective, if not effectively achieved, can have significant health consequences for a patient.

One existing button design has been characterized as a "dog bone". This button has lengthwise ends with oppositely opening slots, one each at the button ends. The button may have some type of holder to simplify application as the surgeon feeds a suture into the two end slots. This design requires that the surgeon apply tension to the suture to draw the U-shaped portion of the suture against the button so that the legs of the "U" do not escape from the end slots and the button is eventually urged against the underlying tissue. Generally, as long as there is tension on the suture, the suture will stay in the end slots.

In this general design, the dog bone button must be made large enough to reduce risk that the suture will escape from one or both of the slots at the button ends as the engaged "U"-shaped portion of the suture tends to expand in width. Generally, the larger the construction, the greater the irritation to any soft underlying tissue. Further, in certain applications, such as at the CMC joint of the thumb, the button pressure must be minimal, whereby even upon completion of a procedure, there remains a tendency of the suture to separate from the button.

The medical field continues to seek improved surgical devices and methods to better address the above areas.

SUMMARY OF THE INVENTION

In one form, the invention is directed to a method of engaging a U-shaped portion of an elongate flexible element with an apparatus to allow the U-shaped portion of the elongate flexible element to act against and thereby maintain a body on the apparatus against part of a human body. The U-shaped portion of the elongate flexible element has a base and first and second legs, with respective first and second lengths, extending in spaced relationship away from the base. The method includes the step of obtaining the apparatus. The body of the apparatus: a) has a tissue abutting side and an opposite side; and b) is capable of being changed between first and second states. The body has an anchoring part and a first channel that extends along a portion of the body up to the anchoring part and has a first entry opening. The method further includes the step of, with the body in the first state, relatively moving the U-shaped portion of the elongate flexible element and body from a starting relationship into an operative relationship wherein the first and second legs straddle the anchoring part and the base can be drawn against the anchoring part to urge the tissue abutting side of the body towards the part of the human body. The step of relatively moving the U-shaped portion of the elongate flexible element and body involves causing at least a part of the U-shaped portion of the elongate flexible element to move through the first entry opening into the first channel and within the first channel up to the anchoring part. The method further includes the step of, with the body in the first state and the body and the U-shaped portion of the elongate flexible element in the operative relationship, changing the body into the second state wherein at least one of: i) a size; and ii) a shape of the first entry opening and/or first channel is changed so as to thereby interfere with movement of the at least part of the U-shaped portion away from the anchoring part within the first channel to and through the first entry opening.

In one form, the step of causing at least a part of the U-shaped portion of the elongate flexible element to move through the first entry opening into the first channel and within the first channel up to the anchoring part involves causing at least one of the first and second legs to move through the first entry opening into the first channel and within the first channel up to the anchoring part.

In one form, the method further includes the step of placing the U-shaped portion of the elongate flexible element under tension with the U-shaped portion of the elongate flexible element and body in the operative relationship to thereby cause the base to be drawn against the anchoring part and the tissue abutting side of the body to be urged against the part of the human body.

In one form, the method further includes the step of securing the elongate flexible element with the elongate flexible element under tension so as to thereby maintain a selected force of the tissue abutting side of the body against the part of the human body.

In one form, the body has a second channel that extends along a portion of the body up to the anchoring part. The step of relatively moving the U-shaped portion of the flexible element and body involves causing the first leg to move within the first channel up to the anchoring part and the second leg to move within the second channel up to the anchoring part.

In one form, the body has a second entry opening spaced from the first entry opening. The step of relatively moving the U-shaped portion of the flexible element and body involves causing the second leg to move through the second entry opening.

In one form, the step of relatively moving the U-shaped portion of the flexible element and body involves causing the first and second legs to move through the first entry opening into the first channel.

In one form, with the body in the first state the first and second channels are in communication with each other.

In one form, with the body in the second state communication between the first and second channels is blocked.

In one form, the method further includes the step of reconfiguring the body by moving a first part of the body relative to another part of the body to thereby change the body from the first state into the second state.

In one form, the step of moving the first part of the body involves deforming the body to thereby change a relationship between the first part of the body and the another part of the body.

In one form, the part of the body and the another part of the body are defined by a single piece.

In one form, with the body in the second state the entry opening is substantially fully blocked so that the at least one of the first and second legs within the first channel is blocked from moving from within the first channel to and through the first entry opening.

In one form, the method further includes the step of changing the body from the first state into the second state by crimping oppositely facing regions of the body.

In one form, the tissue abutting side of the body has a first substantially flat surface.

In one form, the opposite side of the body has a second substantially flat surface. The first and second substantially flat surfaces reside in first and second planes that are substantially parallel.

In one form, the elongate flexible element is a suture.

In one form, the first part is a cantilevered part.

In one form, the apparatus includes an elongate handle fixed to the body. The method further includes the step of repositioning the body through manipulation of the handle.

In one form, the method further includes the step of separating the handle from the body.

In one form, the step of separating the handle from the body involves breaking a frangible connection between the handle and the body.

In one form, the method further includes the step of reconfiguring the body using a crimping tool to change the body from the first state into the second state.

In one form, the crimping tool is a surgical needle holder.

In one form, the method further includes the step of, with the U-shaped portion of the flexible element and body in the operative relationship, advancing the body into a passage in the part of the human body, as an incident of which the body is changed from the first state into the second state.

In one form, the invention is directed to the combination of: an elongate flexible element that can be directed into a human body tissue and configured to define a U-shaped portion projecting from the human body tissue; and an apparatus having a body with a tissue abutting side and an opposite side. The U-shaped portion has a base and first and second legs projecting in spaced relationship away from the base, with the legs each having a length extendable into the human body tissue. The body has first and second channels and an anchoring part with a bearing surface between the first and second channels. The first and second channels respectively have first and second entry openings. The body is configured so that the body and elongate flexible element can be relatively moved from a starting relationship so as to cause: a) a midlength part of the first leg to move through the first entry opening into the first channel; b) a midlength part of the second leg to move through the second entry opening into the second channel; and c) the base of the U-shaped portion to overlie the bearing surface, whereupon the U-shaped portion and body are in a preliminary operative relationship. The body is configured so that with the U-shaped portion and body in the preliminary operative relationship, the body blocks movement of both the first leg out of the first channel and the second leg out of the second channel by movement of the first and second legs away from each other in a single plane. With the U-shaped portion and body in the preliminary operative relationship, the elongate flexible element can be moved to cause the U-shaped portion and body to be changed into a final operative relationship wherein the base of the U-shaped portion is moved against the bearing surface.

In one form, the body has an S-shaped portion extending around portions of the first and second channels.

In one form, the anchoring part has an elongate member with a length extending in a first line. A reference plane orthogonal to the line does not extend through both the first and second entry openings.

In one form, the anchoring part is defined by an elongate member with a length extending in a first line. A reference plane orthogonal to the first line does not extend through either of the first and second entry openings.

In one form, the apparatus further includes an elongate handle fixedly connected to the body which can be grasped and repositioned to move the body.

In one form, the elongate handle is joined to the body through a frangible connection.

In one form, the entry openings each has an entry width. The length of the elongate member is greater than the entry width of each of the first and second receptacles.

In one form, the first and second entry openings are on opposite sides of a reference plane bisecting the length of the elongate member and orthogonal to the first line.

In one form, the tissue abutting side of the body is defined by a substantially flat surface.

In one form, the body is made from a metal material.

In one form, the invention is directed to the combination of: an elongate flexible element that can be directed into a human body tissue and configured to define a U-shaped portion projecting from the human body tissue; and an apparatus having a body with a tissue abutting surface. The U-shaped portion has a base and first and second legs projecting in spaced relationship away from the base, with the legs each having a length extendable into the human body tissue. The apparatus includes an anchoring part. A first channel extends along a portion of the body up to the anchoring part. The apparatus is configured so that with the body in a first state, the U-shaped portion of the elongate flexible element and body can be relatively moved from a starting relationship into an operative relationship wherein the first and second legs straddle the anchoring part and the base can be drawn against the anchoring part to urge the first surface of the body towards the part of the human body, as an incident of which at least a part of the U-shaped portion of the elongate flexible element is caused to move through the first entry opening into the first channel and within the first channel up to the anchoring part. The body has a part that is movable towards another part of the body to thereby place the body in a second state wherein at least one of: i) a size; and ii) a shape of the first entry opening and/or first channel is changed so as to thereby interfere with movement of the at least part of the U-shaped portion away from the anchoring part within the first channel to and through the first entry opening.

In one form, the body has a second channel that extends along a portion of the body up to a second entry opening.

In one form, the movable part of the body is movable by deforming the body.

In one form, the movable part is a cantilevered part that is deformable.

In one form, the body has a second channel that extends along a portion of the body up to the anchoring part.

In one form, the body has a second entry opening to the second channel.

In one form, the body has a second part that is movable towards another part of the body to thereby at least one of change: a) a size; and b) a shape of the second entry opening and/or second channel.

In one form, the body is "U"-shaped.

BRIEF DESCRIPTION OF THE DRAWINGS

FIG. 16 is an exploded, perspective view of another form of instrument body, according to the present invention, with U-shaped portions on an elongate flexible element and the body in a starting relationship;

FIG. 17 is a view as in FIG. 16 wherein separate U-shaped portions on the elongate flexible element and the body are in an operative relationship with the body in the FIG. 16 state;

FIG. 18 is a view as in FIG. 17 wherein the body is crimped to change the state thereof from that shown in FIGS. 16 and 17;

DETAILED DESCRIPTION OF THE PREFERRED EMBODIMENT

Figure 1:
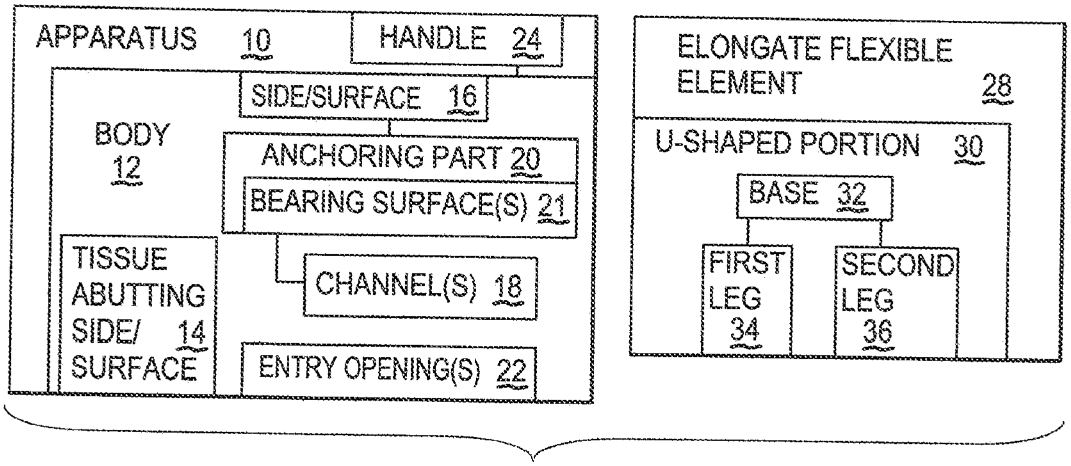
FIG. 1 is a schematic representation of an apparatus for supporting a U-shaped portion of an elongate flexible element against a human body tissue, with the elongate flexible element with which the apparatus is used shown also in schematic form.

In FIG. 1, an apparatus 10 is shown, in schematic form, consisting of a body 12 with a tissue abutting side/surface 14 and an opposite side/surface 16. The tissue abutting side 14 may be substantially flat or contoured to a tissue surface it is designed to engage. The body 12 has at least one channel 18 extending along a portion of the body 12 up to an anchoring part 20. The at least one channel 18 has an entry opening 22. With multiple channels 18, separate or shared entry openings may be provided. The anchoring part 20, which may be made up of one or more pieces, defines at least one bearing surface 21.

A graspable handle 24 is optionally provided and fixed to the body 12 to facilitate repositioning and handling thereof.

Also shown schematically in FIG. 1 is an elongate flexible element 28, used in combination with the apparatus 10. The elongate flexible element 28 may be any elongate flexible element typically surgically connected to human body tissue, whether soft or hard, and which in use has a U-shaped portion 30 projecting from a passage in tissue and which is required to be controlled at the tissue side so as not to be drawn back into and through the passage. The U-shaped portion 30 typically makes up part of a closed loop. However, this is not a requirement. The schematic showing of the elongate flexible element 28 is intended to encompass virtually any type of elongate flexible element used in medical procedures and that passes through a single tissue or multiple tissues. For purposes of simplicity, the elongate flexible element 28 will be identified through the description and claims herein as a suture, with it understood that this is a representative construction which is intended to be equivalent to any elongate flexible element used in surgical procedures such as, for example, without limitation, a tendon graft, etc.

The apparatus 10 is configured to cooperate with the U-shaped portion 30 that projects from a tissue passage. The U-shaped portion 30 consists of a base 32 and first and second legs 34, 36, respectively, that project in spaced relationship away from the base 32. Each of the legs 34, 36 has a length.

The body 12 is configured so that the body 12 and U-shaped portion 30 of the elongate flexible element 28 can be relatively moved from a starting relationship, which may be a fully separated relationship, into an operative relationship wherein the first and second legs 34, 36 straddle the anchoring part 20 and the base 32 can be drawn against the bearing surface 21 on the anchoring part 20 to urge the tissue abutting side 14 of the body 12 towards a part of the human body.

The body 12 may be used in a single state or reconfigured to be changed from a first state into a second state to thereby change size and/or shape of one or more of the entry openings 22 and/or channels 18 to avoid inadvertent partial or full separation of the U-shaped portion 30 from the body 12.

In another form, no reconfiguration of the body 12 is necessarily carried out—but could be. The body 12 in one such version is configured so that with the U-shaped portion 30 in a preliminary operative position, the body 12 blocks movement of the first leg 34 out of a first channel **18*a* and movement of the second leg 36 out of a second channel 18*b* by movement of the first and second legs 34, 36** away from each other in a single plane.

With this construction, the elongate flexible element 28 in the preliminary operative position can be moved to cause the U-shaped portion 30 to be changed into a final operative position wherein the base 32 of the U-shaped portion 30 acts against the bearing surface 21 thereby to urge the tissue abutting side 14 of the body 12 against or toward the human body tissue in which the passage is formed.

In certain procedures, the body 12 will be drawn against tissue that is in turn urged against another body part. In other procedures, the body 12 limits a distance an associated tissue can move away from another body part. In the latter case, with the U-shaped portion 30 in the final operative position, the body 12 may be urged with limited pressure against the associated tissue or may be spaced fully from the associated tissue and engaged therewith only to stabilize the associated tissue or limit movement of the associated tissue away from another body part. The invention encompasses both types of procedures but will be described throughout principally relative to the former.

The schematic representation in FIG. 1 is intended to encompass virtually an unlimited number of different configurations for each of the components depicted therein and their interaction. The description hereinbelow is intended to be representative only of certain structures and method steps that can be performed according to the invention.

Figure 2:
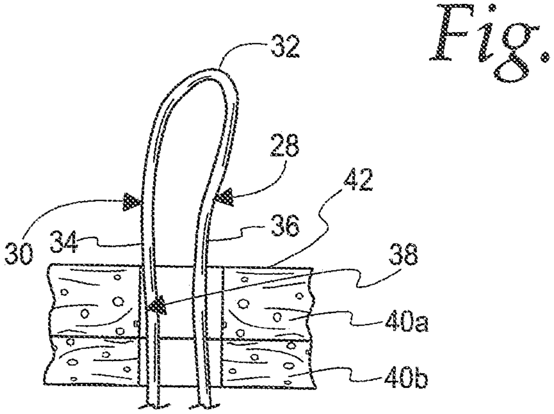
FIG. 2 is a fragmentary, partial cross-sectional view of a tissue with a passage and an elongate flexible element, in the form of a suture, having a U-shaped portion projecting through the passage and required to be controlled by being blocked from being drawn into and through the passage.

FIG. 2 shows a typical U-shaped portion 30 on an elongate flexible element/suture 28. The U-shaped portion 30 consists of the aforementioned base 32 and first and second elongate legs 34, 36. The U-shaped portion 30 is directed through a passage 38, in this case defined through two different overlying tissues **40*a*, 40*b***. As noted above, the invention might be practiced with a single tissue, multiple tissues that may be all hard tissue, soft tissue, or a combination of hard and soft tissue.

The invention is concerned with controlling the U-shaped portion 30 of the suture 28 that projects from the passage 38 beyond the tissue surface 42.

The suture 28 can be configured in the "U" shape in different manners. For example, the suture 28 might simply be folded against itself, whereupon the suture 28 can be directed through the passage 38, as by leading with the base 32, until it is exposed through and at the tissue surface 42.

Figure 3:
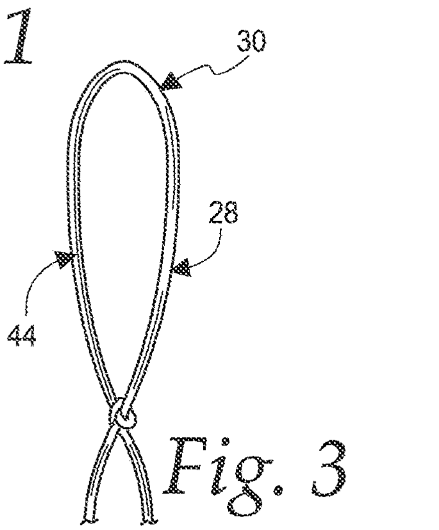
FIG. 3 is a view of a suture formed into a continuous loop as to produce the U-shaped portion in FIG. 2.

In FIG. 3, the suture 28 is tied as conventionally carried out to produce a closed loop 44, wherein the U-shaped portion 30 is defined on a part of the loop 44 and manipulated in the same manner as described with respect to FIG. 2.

There is no limitation as to how the U-shaped portion 30 might be formed or how the suture 28 might be controlled to produce the FIG. 2 arrangement.

Figure 4:
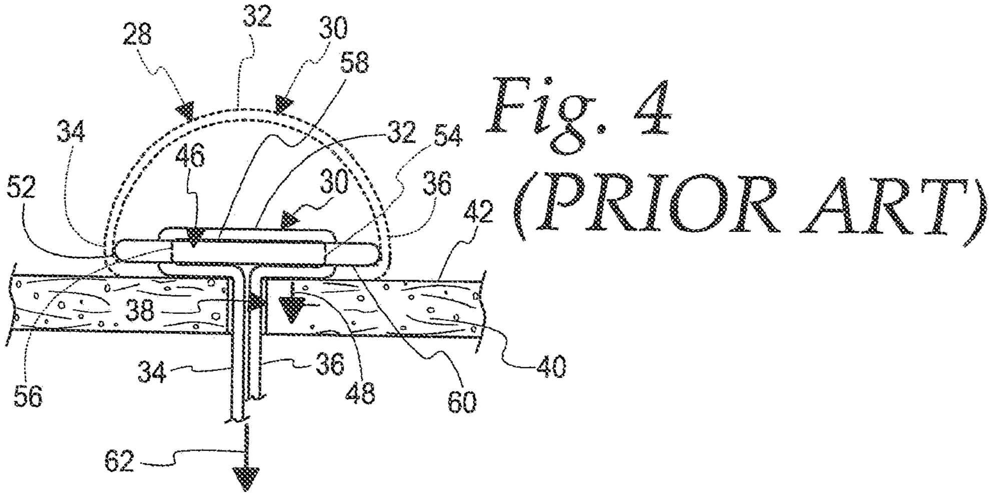
FIG. 4 is a view as in FIG. 2 with a prior art apparatus shown connected to the projecting U-shaped portion to prevent drawing of the U-shaped portion into and through the passage.
Figure 5:
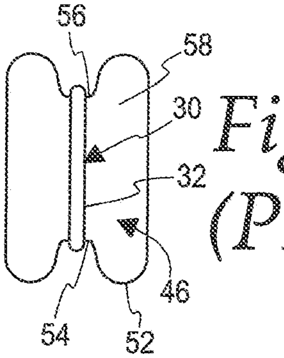
FIG. 5 is a plan view of the apparatus in FIG. 4 with the suture wrapped thereagainst.

In FIGS. 4 and 5 a conventional "button", as described in the Background section herein, is shown at 46 to engage the U-shaped suture portion 30 to prevent the U-shaped portion 30 from being drawn back in the direction of the arrow 48 through the passage 38 in the tissue 40.

The button 46 consists of an elongate body 52 with oppositely opening U-shaped slots 54, 56, one each at its spaced ends.

To operatively engage the button 46 with the U-shaped portion 30 of the suture 28, the width of U-shaped portion 30 is enlarged adequately, as shown in dotted lines, to allow the legs 34, 36 to be fit, one each, into the slots 54, 56 with the base 32 spanning between the slots 54, 56 over the side 58 that faces oppositely to a side 60 which abuts to the tissue side 42.

By then tensioning the suture 28 by drawing the legs 34, 36 in the direction of the arrow 62 through the passage 38, the U-shaped portion 30 reconfigures, whereupon the base 32 ultimately conforms to, and abuts the surface 58 substantially fully between the slots 54, 56. Continued drawing of the legs 34, 36 causes the suture 28 to be drawn forcibly into the slots 54, 56 and the base 32 to be drawn against the body 52, thereby stabilizing the body and/or urging the side 60 against the tissue 40. The enlarged shape of the elongate body 52 prevents its migration into the passage 38, whereupon the tensioned U-shaped portion 30 is controllably fixed at the tissue surface 42 and distributes the tensioning forces over the area of the side 60.

As noted above in describing the conventional "dog bone" button, with the suture 28 in the dotted line position in FIG. 4, the slackened and widely spaced suture legs 34, 36 are only loosely aligned with their respective slots 54, 56, even if an effort is made to somewhat constrict the width of the U-shaped portion 30. Thus, the surgeon is required to pull on the suture legs 34, 36 and at the same time prevent inadvertent shifting of the legs 34, 36 out of alignment with their respective slots 54, 56. This may be a challenge that complicates the procedure and, as noted above, potentially frustrates and fatigues the surgeon. Still further, the open nature of the slots 54, 56 is such that the natural enlargement of the U-shaped portion 30, under residual forces developed during bending, tends to move the legs 34, 36 thereof out of their respective slots 54, 56. Ultimately, multiple attempts may be required to place the suture 28 and button 46 in a proper operative relationship. There is a further potential that the open shape of the slots 54, 56 may result in the suture legs 34, 36 being inconsistently seated therein. This may result in a post-surgical loosening and potential separation of the suture 28 from its intended operative position, particularly when a procedure does not require that the U-shaped portion 30 be highly constricted or that the suture 28 defining the U-shaped portion 32 be placed under a relatively high tension.

One specific, exemplary form of the inventive apparatus 10 will now be described with reference to FIGS. 6-12.

Figure 7:
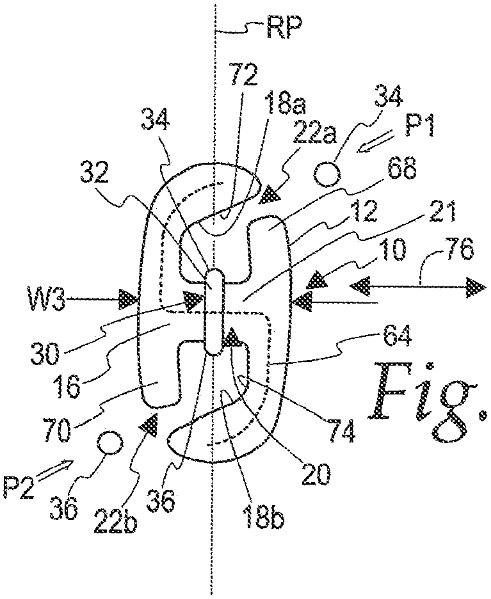
FIG. 7 is a plan view of the body on the apparatus in FIG. 6, with the handle thereon removed, and with the suture in a final operative position.

The body 12 of the apparatus 10, as viewed from above, has an overall "S" shape, as approximated by the dotted line 64 in FIG. 7. This "S" shape extends around a first channel 18*a* and second channel 18*b* that have entry openings 22*a,* 22*b,* respectively. The body 12 has an elongate member/bar defining the anchoring part 20. The bearing surface 21 is defined on the anchoring part 20 between the channels 18*a,* 18*b.*

Cantilevered parts 68, 70 project in opposite directions away from the ends of the elongate bar shape, one each towards the free ends of the "S", to thereby establish the width dimension W1, W2 of the entry openings 22*a,* 22*b,* respectively.

Figure 6:
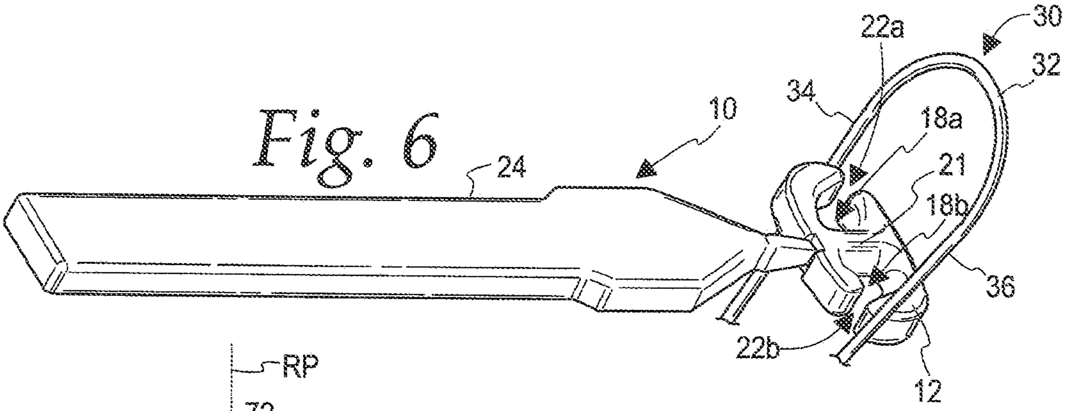
FIG. 6 is a perspective view of the inventive apparatus with a U-shaped portion of a suture aligned to be moved into a preliminary operative position, and with a graspable handle usable to reposition a body on the apparatus.
Figure 8:
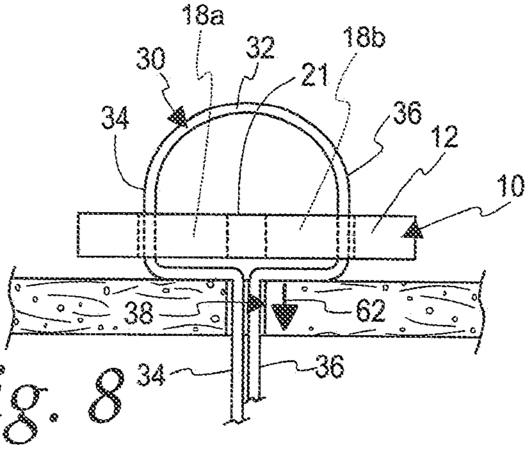
FIG. 8 is a view as in FIG. 4 with the U-shaped portion of the suture in the preliminary operative position with respect to the inventive apparatus body.

The body 12 is configured so that, as seen in FIGS. 6 and 7, midlength parts of the first and second legs 34, 36 must move oppositely in paths P1, P2, each in a line that is non-parallel to a vertical reference plane RP bisecting the width W3 of the body 12, and length of the anchoring part 20, to allow the legs 34, 36 to enter the channels 20*a,* 20*b* through the entry openings 22*a,* 22*b,* whereby the base 32 overlies the bearing surface 21 as seen in FIG. 8—representing one preliminary operative position for the U-shaped portion 30.

Figure 9:
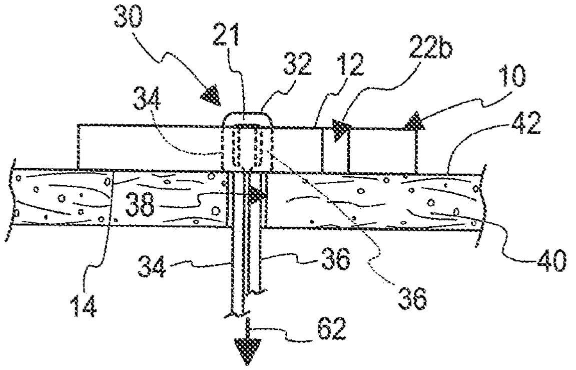
FIG. 9 is a view as in FIG. 8 wherein the U-shaped portion is changed to the final operative position of FIG. 7.

With the legs 34, 36 extending through the tissue passage 38 and starting with the U-shaped portion 30 wrapped over/against the elongate anchoring part 20 in the preliminary operative position in FIG. 8, the legs 34, 36 are drawn in the direction of the arrow 62 to bear the base 32 of the suture 28 against the bearing surface 21, whereupon the U-shaped portion 30 assumes its final operative position, as shown in FIGS. 7 and 9, wherein the tissue abutting side 14 of the body 12 is drawn firmly against the tissue surface 42.

As a result, the U-shaped portion 30 maintains the body 12 positively against the tissue surface 42. With the inventive construction, once the legs 34, 36 are placed in their respective channels 18, 20, they are not prone to escaping therefrom by expansion of the width of the U-shaped portion 30, with the U-shaped portion 30 in a single plane, as is possible with the prior art structure as shown in FIGS. 4 and 5. More particularly, expansion of the U-shaped portion 30 in the reference plane in FIG. 7 causes the leg 34 to abut to a surface portion 72 surrounding the channel 18*a,* with the leg 36 abutting to a surface portion 74 bounding the channel 18b.

As seen in FIG. 7, the elongate anchoring part 20 has a length extending in a first line indicated by the double-headed arrow 76 which is orthogonal to the reference plane RP. With the reference plane RP bisecting the length of the anchoring part 20, the openings 22*a,* 22*b* reside on opposite sides thereof. The reference plane RP does not pass through either of the entry openings 22*a,* 22*b.* This is true even if the reference plane is shifted to either end of the anchoring part 20.

Further, even if the plane of the U-shaped portion 30 is shifted to be non-orthogonal to the length of the anchoring part 20, that plane will not pass through both of the entry openings 22*a,* 22*b.*

Accordingly, for either of the legs 34, 36 to escape from a respective opening 22*a,* 22*b,* the legs 34, 36 must be moved in an oblique path, oppositely to the direction indicated by the arrows P1, P2.

Whereas the U-shaped portion 30 of the suture 28 can be simply enlarged to align with the prior art button 46 and thereafter restricted to arrive at a final state, placement of the legs 34, 36 in respective channels 18*a,* 18*b* and engagement of the base 32 of the U-shaped portion with the anchoring part 20 require that the body 12 and suture 28 be relatively repositioned through different changes in suture shape and/or angular relationship between the suture 28 and body 12. As a result, the U-shaped portion 30 is not prone to accidentally separating from the body 12. At the same time, placement of the suture and apparatus 10 in operative relationship can be efficiently accomplished by controllably moving one or both of the suture 28 and body 12. This relative movement can be effected by manipulating primarily the suture 28 or the body 12 or by coordinatingly moving both.

As one example, the U-shaped portion 30 can be aligned generally as shown in FIG. 6, which allows the leg 34 to be directed through the entry opening 22, whereupon the body 12 can be angularly repositioned to align the leg 36 with the entry opening 24. Once the legs 34, 36 are directed through their respective openings 22, 24 into the channels 18*a,* 18*b* and to against the anchoring part 20, the legs 34, 36 can be drawn to urge the base 32 to against the anchoring part 20.

Of course, it is contemplated that the free ends of the suture legs 34, 36 might be directed into the channels 18*a,* 18*b* to place the U-shaped portion 30 in its preliminary operative position.

As shown in FIG. 8, once the midlength part of the first leg 34 is moved through the entry opening 22a into the channel 18*a* and the midlength part of the second leg 36 is moved through the second entry opening 22b into the channel 18b, the base 32 overlies the bearing surface 21 on the anchoring part and the U-shaped portion 30 is in the preliminary operative position.

By then drawing the legs 34, 36 away from the passage in the direction of the arrow 62, the U-shaped portion 30 is changed to the final operative position of FIGS. 7 and 9, wherein the base 32 is drawn against the bearing surface 21 to thereby urge the tissue abutting side 14 of the body 12 against the surface 42 of the body tissue 40.

As seen most clearly in FIG. 6, all edges of the body 12 are rounded to avoid hang-up of a suture as the suture 28 is slid thereagainst. At the same time, this reduces the likelihood that any edge against which the suture 28 bears might be compromised or severed during a procedure or over time with body tissue shifting after the procedure is completed.

Further, the relatively small effective diameter of the elongate member 66 may reduce the severity of bending of the suture 28 to allow it to conform to the anchoring part 20 and the legs 34, 36 thereon to be directed thereaway into the passage 38.

To further reduce the likelihood of any part of the suture 28 unintentionally being separated from the body 12 once the U-shaped portion is in the preliminary operative position, the body 12 may be reconfigured to change a dimension and/or shape of at least one of the entry openings 22*a,* 22*b*. This may be accomplished in many different manners, as by providing separate parts guided in controlled relative movement, providing a reduced dimensional or otherwise locally weakened location that allows controlled movement of one part relative to another part of the body 12 through deformation, etc.

Figure 10:
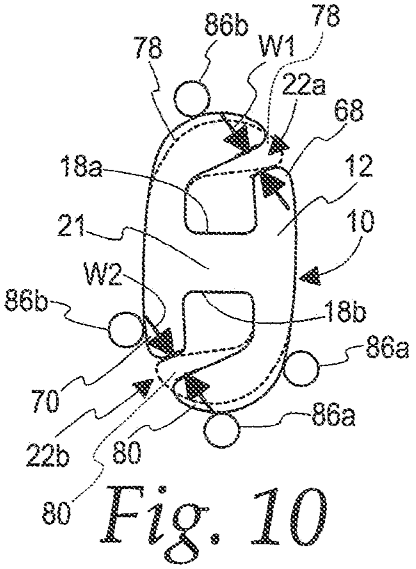
FIG. 10 is a view as in FIG. 7 wherein parts of the body have been deformed to change shape and dimension of entry openings to channels on the body and the channels.

As seen in the exemplary form in FIG. 10, the body 12 may be deformed by moving opposite, integrally formed, lengthwise, cantilevered end parts 78, 80 towards or against the cantilevered arms 68,70, respectively, to either reduce the widths W1, W2 of the entry openings 22*a,* 22*b,* or, as shown in dotted lines, effectively eliminate these entry openings 22*a,* 22*b* to define a fully surrounded channel 18*a,* 18*b*. In this exemplary form, the starting width W1, W2 of each entry opening 22, 24 is less than the length of the anchoring part 20. This deformation may also change shape and size of the channels 18*a,* 18*b.*

Figure 12:
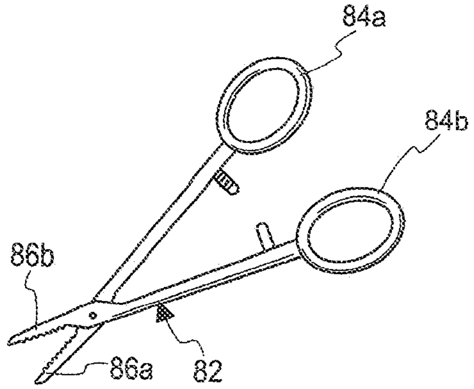
FIG. 12 is a plan view of a conventional surgical needle holder usable to reconfigure the body as shown in FIG. 10.

In one form, the reconfiguring of the body 12 can be accomplished through a conventional surgical needle holder, as shown at 82 in FIG. 12. The needle holder 82 has separate looped handles 84*a,* 84*b* that can be manipulated to move jaws 86*a,* 86*b* towards each other to effect a crimping action.

The body 12 may be situated so that its length is captured between the jaws 86*a,* 86*b* before pressure is applied, which simultaneously alters the entry openings 22*a,* 22*b.* Alternatively, as shown at the bottom of the body in FIG. 10, the width of the body 12 may be grasped and crimped to individually close the entry openings 22*a,* 22*b* in separate steps.

The crimping may produce a randomly deformed shape, or the deformation may be controlled by strategically selecting shapes, thicknesses, etc., or by locally weakening material so that a predictable collapse or reconfigured shape results that is maintained without risk of tending back to a starting configuration that might compromise maintenance of the suture upon the body 12 in a desired end relationship.

The invention contemplates reconfiguring body shapes other than those having the preferred body shapes described herein, or a similar body shape. For example, reconfiguration of a "dog bone" body shape with open receptacles/channels might reduce the likelihood of inadvertent separation of an operatively positioned U-shaped suture portion.

To further assist manipulation of the body 12, an elongate handle 24 is attached thereto and can be grasped and moved to reposition the body 12. The handle 24 and body 12 can be made to move as one piece.

Figure 11:
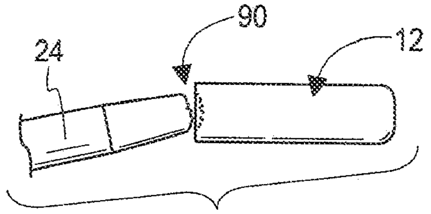
FIG. 11 is a fragmentary, side view showing a frangible connection between the handle and body in FIG. 6 once the handle has been broken away from the body.

As shown in FIG. 11, a frangible connection may be provided at 90 between the handle 24 and body 12, whereupon the handle 24 can be broken away and separated from the body 12 once the body 12 is in its final stabilized position. The breakaway location may be recessed within the body 12 so that no residual rough edges are formed that might irritate a patient's tissue.

To afford the desired integrity and allow reconfiguration of the body 12, it is preferably made from a strong but deformable material such as metal, and in one preferred form an alloy of titanium, pure titanium, stainless steel, or other metal. Of course, the precise material making up the body 12 is not so limited.

Figure 13:
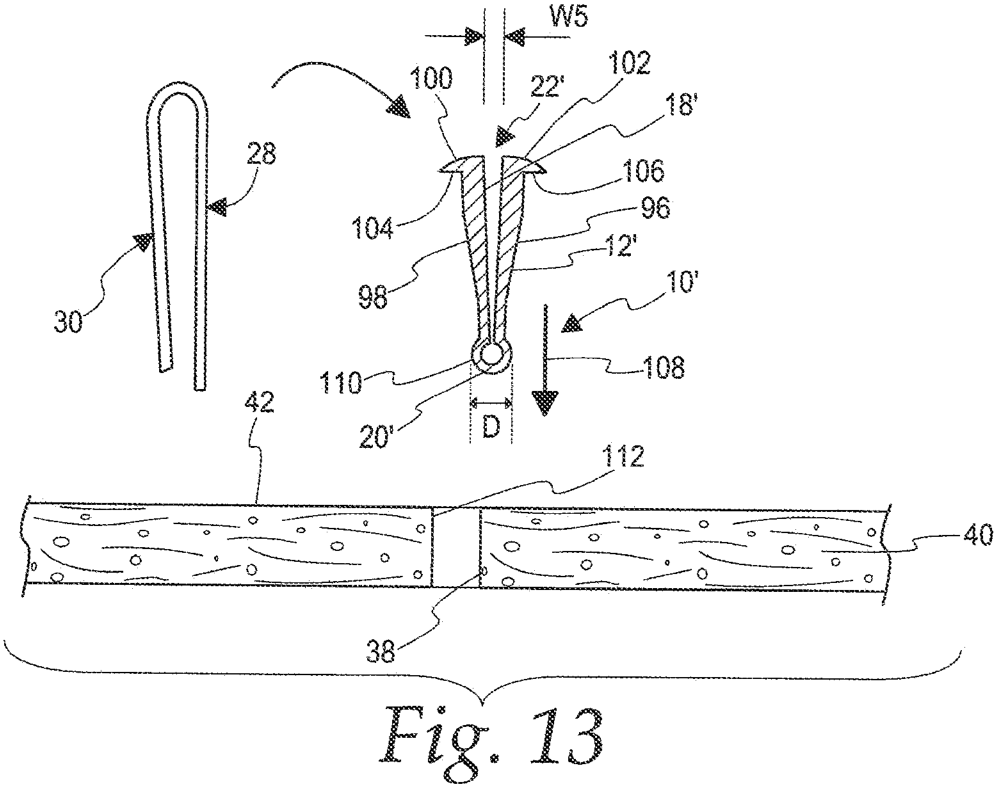
FIG. 13 is an exploded, partially schematic representation of another form of instrument, according to the present invention, with a body thereon in a first state and in relationship to an elongate flexible component and a tissue with a passage therethrough.
Figure 14:
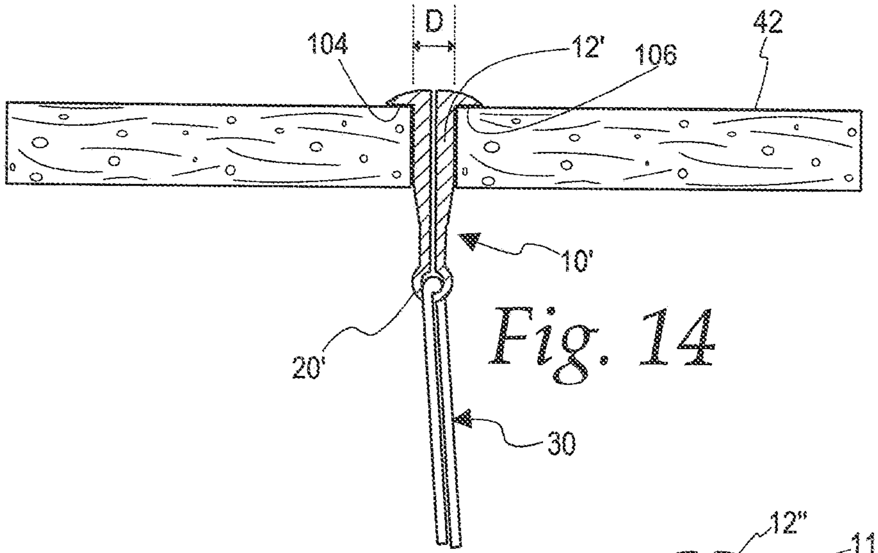
FIG. 14 is a view as in FIG. 13 with the components assembled and the body directed through the tissue passage and in a second state.

In FIGS. 13 and 14, a modified form of apparatus is shown at 10'. The body 12' has an overall "U" shape with an anchoring part 20' at the base of the "U" and two legs 96, 98 projecting away from the anchoring part 20' and bounding a channel 18' with an entry opening 22'. The legs 96, 98 are elongate, each widening in an upward direction in FIG. 13, and have offset free ends 100, 102, further respectively defining generally flat tissue engaging surfaces 104, 106.

In FIG. 13, the U-shaped portion 30 of the elongate flexible element 28 and the body 12' are in a starting relationship, in this case in a fully spaced relationship. In FIG. 13, the body 12' is shown in a first state wherein the entry opening 22' has a first width W5. The U-shaped portion 30 of the elongate flexible element 28 and body 12' are relatively moved to cause a part of the U-shaped portion 30 to move through the entry opening 22' into the channel 18' and within the channel 18' up to the anchoring part 20', until the operative relationship shown in FIG. 14 is realized.

The body dimension D in the region of anchoring part 20 is slightly less than the diameter of a passage 38 formed through tissue 40.

By drawing the body 12' in the direction of the arrow 108, the then leading portion 110, including the anchoring part 20' with the U-shaped portion 30 thereagainst, can be advanced through the passage 38. As this occurs, the legs 96, 98, by reason of their increasing width, are wedged by the surface 112 surrounding the passage 38, progressively reducing the width of the entry opening 22', until the entry opening 22' is effectively blocked, and the channel 18' effectively closed, so that the U-shaped portion 30 cannot move away from the anchoring part 20', through the channel 18' up to and from the entry opening 22'. Thus, as an incident of moving the body 12' into the passage 38, the body 12' changes from the first state into a second state.

Once the body 12' is fully seated, the surfaces 104, 106 abut to the tissue surface 42 to maintain a consistent position thereof. The wedged legs 96, 98 positively frictionally maintain the body 12' within the passage 38.

Figure 15:
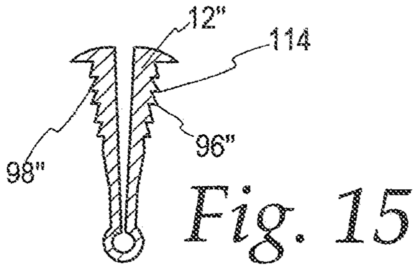
FIG. 15 is a view corresponding to that in FIG. 13 of a modified form of body in the same state as in FIG. 13.

In FIG. 15, a modified form of body is shown at 12" which includes legs 96", 98", corresponding to the legs 96, 98 in FIGS. 13 and 14 with roughening, as by incorporation of ribs 114 to more aggressively grip the tissue surface 112 to effect a more positive engagement.

Another form of the body is shown in FIGS. 16-18 at 12'''. The body 12''' is in the form of a ring which may have a circular shape or another shape, such as elliptical, etc. The body 12''' has a perimeter wall portion 116 that extends around first and second channels 18*e,* 18*b*''' and is interrupted to define an entry opening 22''' in communication with the first channel 18*a*".

An anchoring part 20' projects in cantilever fashion from a first region 120 of the wall portion 116 generally diametrically oppositely to separate the channels 18*a*''', 18*b*''' from each other.

With the body 12" in a first state, as seen in FIGS. 16 and 17, a free end 122 of the anchoring part 20''' is spaced from the perimeter wall portion 116, whereby a gap 124 is formed that communicates between the channels 18*a*''',18*b*'''.

In FIG. 16, the elongate flexible element 28 is bent against itself at 126 so as to effectively define separate U-shaped portions 30*a*", 30*b*''' that straddle the anchoring part 20''', as shown in FIG. 17. Alternatively, the single U-shaped portion may remain unbent and be placed into operative relationship with the body 12''' in that form.

The multiple U-shaped portions 30a", 30b''' are both introduced through the entry opening 22" with the first legs 34*a*", 34*b*" moving in the first channel 18*a*''' up to one side 128 of the anchoring part 20'''. The second legs 36*a*", 36*b*''' travel through the first channel 18*a*''' past the free end 122 into the second channel 18*b*" to reside at the side 130 of the anchoring part 20 opposite the side 128.

As shown in FIG. 18, the body 12''' can be changed from the first state, shown in FIGS. 17 and 18, into a second state by crimping diametrically opposite regions under pressure between two spaced parts 134, 136. This crimping action deforms the body 12''' to cause one part 138 thereof to move relative to another part 140 thereof which can be done to an extent to either reduce the size of the entry opening 22 or substantially fully block the same.

With a single U-shaped portion formed, that U-shaped portion may be moved relative to the body 12''' in its first state from a starting relationship by initially engaging the U-shaped portion at the free end of the one part 138 or the free end 124 of the anchoring part 20'''

Figure 19:
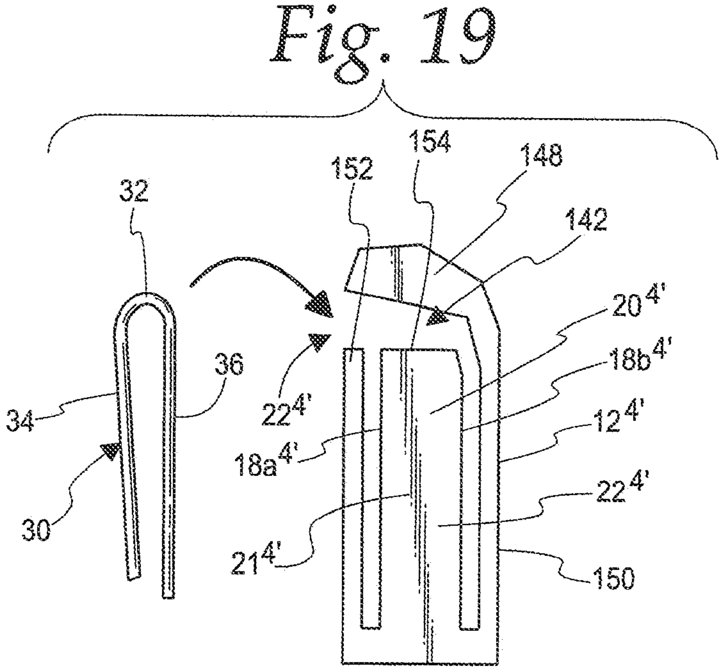
FIG. 19 is an exploded, partially schematic representation of a further form of instrument body, according to the present invention, in a starting relationship with a U-shaped portion on an elongate flexible element.
Figure 20:
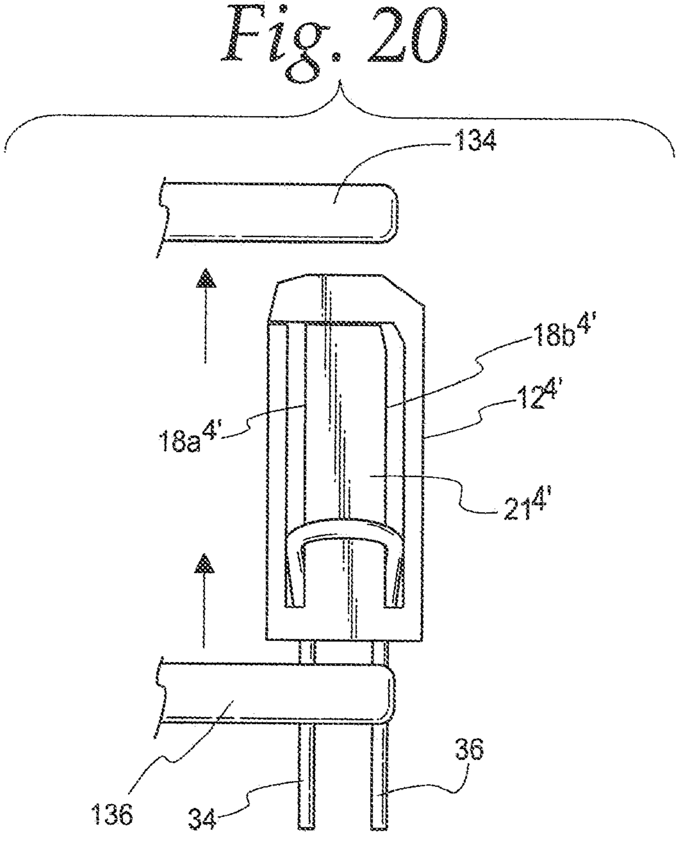
FIG. 20 is a view as in FIG. 19 wherein the U-shaped portion of the elongate flexible element and body have been placed in an operative relationship and the body has been reconfigured to change the state thereof.

Another form of the inventive body is shown at 12$^{4'}$ in FIGS. 19 and 20.

The body 12$^{4'}$ has a substantially flat shape that, with the body 12$^{4'}$ in a first state as in FIG. 19, defines a cantilevered anchoring part 20$^{4'}$ between first and second channels 18*a*$^{4'}$, 18*b*$^{4'}$. With the body 12$^{4'}$ in the first state of FIG. 19, the channels 18*a*$^{4'}$, 18*b*$^{4'}$ are in communication with each other through a gap region 142.

A single entry opening 22$^{4'}$ allows direction of suture legs 34, 36 into the channels 18*a*$^{4'}$, 18*b*$^{4'}$, respectively, whereby the base 32 projects across a bearing surface 21$^{4'}$ on the anchoring part 20$^{4'}$.

More specifically, in changing from a starting relationship as shown in FIG. 19, the elongate flexible component 32 and body 12$^{4'}$ are relatively moved to cause the leg 36 to move through the entry opening 22$^{4'}$ and the gap 142 and into the channel 18*b*$^{4'}$. The leg 34 moves through the entry opening 22$^{4'}$ into the channel 18*a*$^{4'}$ without having to move into the gap 142.

Once the U-shaped portion of the elongate flexible element 32 and body are placed into the operative relationship a free end region 148 on a cantilevered part 150 is moved to bridge separate parts 152, 154 on the body 12$^{4'}$, thereby to eliminate the gap 142, and at the same time block the entry opening 22$^{4'}$.

This deformation of the body 12$^{4'}$ can be effected in different manners and preferably as by a crimping action through parts as those 134, 136, described for the prior embodiment.

With the body 12$^{4'}$ in the second state of FIG. 20, the communication between the channels 18*a*$^{4'}$, 18*b*$^{4'}$ is eliminated, although this is not a requirement.

The foregoing disclosure of specific embodiments is intended to be illustrative of the broad concepts comprehended by the invention.

The invention claimed is:

1. A method of engaging a U-shaped portion of an elongate flexible element with an apparatus to allow the U-shaped portion of the elongate flexible element to act against and thereby maintain a body on the apparatus against part of a human body, the U-shaped portion of the elongate flexible element having a base and first and second legs, with respective first and second lengths, extending in spaced relationship away from the base, the method comprising the steps of:

obtaining the apparatus, the body of the apparatus: a) having a tissue abutting side and an opposite side; and b) capable of being changed between first and second states, the body comprising an anchoring part and a first channel that extends along a portion of the body up to the anchoring part and has a first entry opening;

with the body in the first state, relatively moving the U-shaped portion of the elongate flexible element and body from a starting relationship into an operative relationship wherein the first and second legs straddle the anchoring part and the base can be drawn against the anchoring part to urge the tissue abutting side of the body towards the part of the human body, wherein the step of relatively moving the U-shaped portion of the elongate flexible element and body comprises causing at least a part of the U-shaped portion of the elongate flexible element to move through the first entry opening into the first channel and within the first channel up to the anchoring part; and with the body in the first state and the body and the U-shaped portion of the elongate flexible element in the operative relationship, changing the body into the second state wherein at least one of: i) a size; and ii) a shape of the first entry opening and/or first channel is changed so as to thereby interfere with movement of the at least part of the U-shaped portion away from the anchoring part within the first channel to and through the first entry opening, wherein the step of causing at least a part of the U-shaped portion of the elongate flexible element to move through the first entry opening into the first channel and within the first channel up to the anchoring part comprises causing at least one of the first and second legs to move through the first entry opening into the first channel and within the first channel up to the anchoring part, wherein the step of relatively moving the U-shaped portion of the flexible element and body comprises causing the first and second legs to move through the first entry opening into the first channel.

2. A method of engaging a U-shaped portion of an elongate flexible element with an apparatus to allow the U-shaped portion of the elongate flexible element to act against and thereby maintain a body on the apparatus against part of a human body, the U-shaped portion of the elongate flexible element having a base and first and second legs, with respective first and second lengths, extending in spaced relationship away from the base, the method comprising the steps of:

obtaining the apparatus, the body of the apparatus: a) having a tissue abutting side and an opposite side; and b) capable of being changed between first and second states, the body comprising an anchoring part and a first channel that extends along a portion of the body up to the anchoring part and has a first entry opening;

with the body in the first state, relatively moving the U-shaped portion of the elongate flexible element and body from a starting relationship into an operative relationship wherein the first and second legs straddle the anchoring part and the base can be drawn against the anchoring part to urge the tissue abutting side of the body towards the part of the human body, wherein the step of relatively moving the U-shaped portion of the elongate flexible element and body comprises causing at least a part of the U-shaped portion of the elongate flexible element to move through the first entry opening into the first channel and within the first channel up to the anchoring part;

with the body in the first state and the body and the U-shaped portion of the elongate flexible element in the operative relationship, changing the body into the second state wherein at least one of: i) a size; and ii) a shape of the first entry opening and/or first channel is changed so as to thereby interfere with movement of the at least part of the U-shaped portion away from the anchoring part within the first channel to and through the first entry opening; and further comprising the step of, with the U-shaped portion of the elongate flexible element and body in the operative relationship, advancing the body into a passage in the part of the human body and as an incident thereof, causing the body to change from the first state into the second state.

3. The method of engaging a U-shaped portion of an elongate flexible element with an apparatus according to claim 2 wherein the body is reconfigured in changing from the first state into the second state.

* * * * *